US006768550B2

(12) United States Patent
Anafi et al.

(10) Patent No.: US 6,768,550 B2
(45) Date of Patent: Jul. 27, 2004

(54) BEAM SHIFTING SURFACE PLASMON RESONANCE SYSTEM AND METHOD

(75) Inventors: David Anafi, Wellington, FL (US); Glen Ramsay, Lakewood, NJ (US); Jeff MacDonald, Little Egg Harbor, NJ (US); Peter Halatin, Howell, NJ (US); Charlie Schwartz, Toms River, NJ (US)

(73) Assignee: Proterion Corporation, Piscataway, NJ (US)

( * ) Notice: Subject to any disclaimer, the term of this patent is extended or adjusted under 35 U.S.C. 154(b) by 0 days.

(21) Appl. No.: 10/206,886

(22) Filed: Jul. 26, 2002

(65) Prior Publication Data

US 2004/0017572 A1 Jan. 29, 2004

(51) Int. Cl.[7] ............................................... G01N 21/55
(52) U.S. Cl. ....................................................... 356/445
(58) Field of Search ................................. 356/445, 446, 356/317, 318, 345; 422/83–89, 61, 68.1, 82.05, 82.11, 82.09; 436/139–142, 144, 164, 165, 170, 171, 113, 121, 131; 250/227.14–227.25, 216

(56) References Cited

U.S. PATENT DOCUMENTS 5,322,798 A * 6/1994 Sadowski .................... 436/113
5,923,031 A * 7/1999 Naya ...................... 250/227.25

* cited by examiner

*Primary Examiner*—Tu T. Nguyen
(74) *Attorney, Agent, or Firm*—Brown Rudnick Berlack Israels LLP; Brian L. Michaelis

(57) ABSTRACT

The invention relates to a surface plasmon resonance system method. The system has at least one light source operable to generate a source beam, a prism having a rear surface at least partially coated with a metallic coating and optionally a dielectric layer. At least one layer under test is positioned on the rear surface of the prism. The source beam is directed at the layer under test thereby defining an angle between the source beam and the rear surface of the prism. A detector is operable to detect light that is reflected or scattered by the layer under test. The source beam is directed towards the layer under test at a selected angle. The source beam is also shifted in at least one plane to illuminate a specific portion of the layer under test based on the selected relative angle and the position of the layer under test on the rear surface of the prism. The rear surface of the prism can be illuminated in one-dimensional or two-dimensional array like fashion.

27 Claims, 8 Drawing Sheets

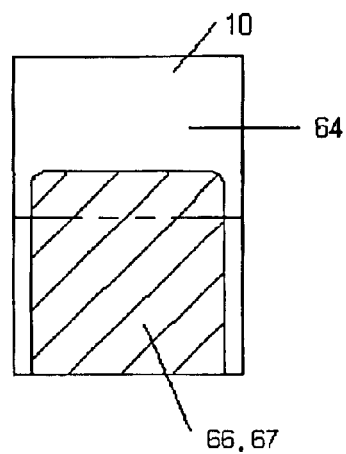 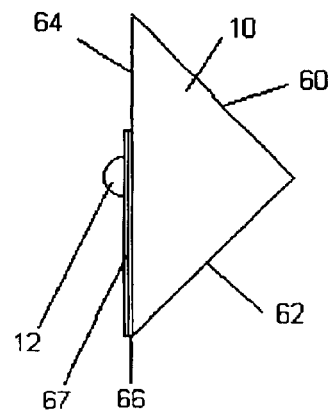
Figure 3          Figure 4
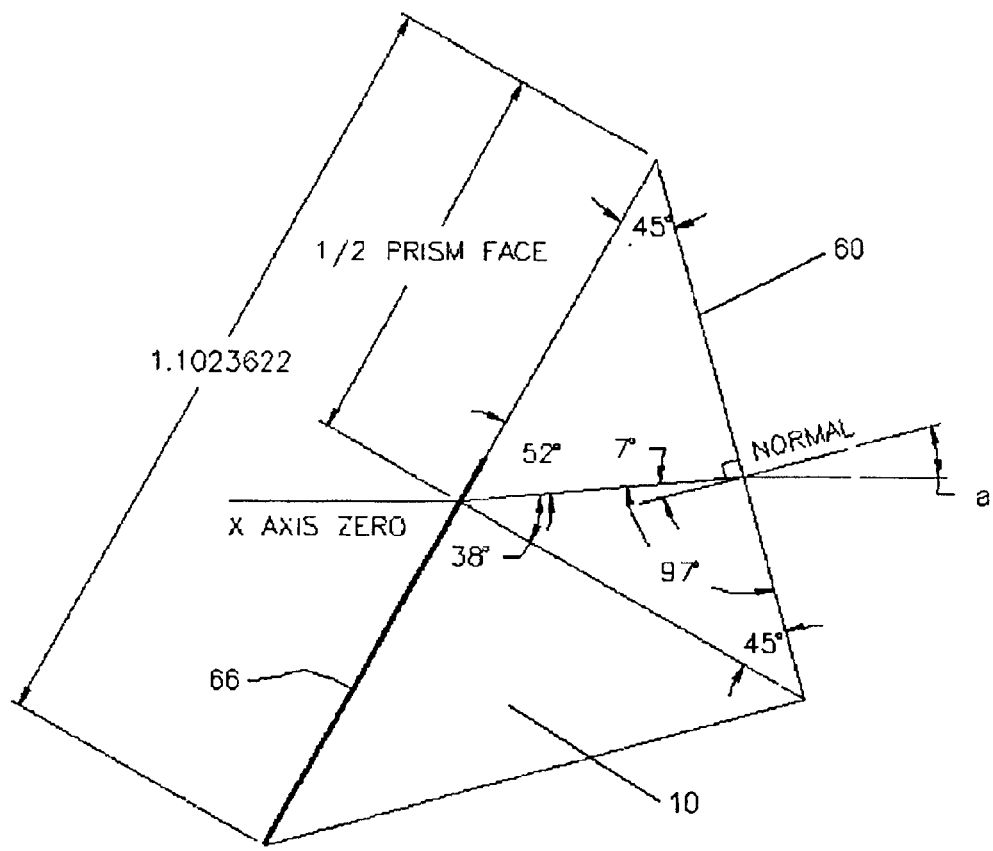
Figure 5

BEAM SHIFTING SURFACE PLASMON RESONANCE SYSTEM AND METHOD

The invention relates to the field of Surface Plasmon Resonance and waveguide phenomena. In particular the invention is directed to beam shifting surface plasmon resonance or plasmon-waveguide resonance systems and methods.

It is understood that when a light-reflecting surface is coated with a thin metallic coating, then light at a specific incident angle can excite the electrons in the metal. This results in localized fluctuations of the electron density known as surface plasmons. The light energy transferred to the metal coating during excitation results in an attenuation of the reflected light intensity. The incident angle and degree of the attenuation depends on the wavelength of the exciting light and the thickness and optical properties of the interface in contact with the metal coating.

The important optical properties of such an interface include the absorbance at the excitation wavelength (extinction coefficient), the refractive index, and the thickness of the interface. The effective distance of Surface Plasmon penetration is only several hundred nanometers (nm) so only the environment at the surface is detected. This property makes Surface Plasmon Resonance (SPR) and Plasmon Waveguide Resonance (PWR) ideal for measuring surface and interfacial chemistry, as well as the properties of thin film coating properties (including molecular films).

It is also understood that gold and silver are two metals that produce strong SPR signals. Under similar conditions the SPR electric field in the sample produced by silver is more than 2 times stronger than gold resulting in much sharper resonances and greater sensitivity. However, the chemical reactivity of silver renders it inappropriate for many applications. Therefore many applications utilize gold as the metallic coating.

PWR is essentially a species of SPR however, PWR techniques utilize one or more dielectric coatings (e.g., silica dioxide) over the metallic coating. The appropriate dielectric coatings serve as both a shield and an "optical amplifier". PWR allows the use of silver as the metallic coating or layer, with its improved optical properties but without suffering from its undesirable chemical properties.

SPR systems utilize specific light polarizations (e.g., p-polarization) in reference to the sample plane to produce resonance signals. In PWR systems, the appropriate dielectric coating also serves as an optical amplifier resulting in additional sharpening of the resonance spectrum, and more importantly, allowing light polarizations both parallel (s-polarization) and perpendicular (p-polarization) to the sample plane to produce resonance signals. For example, a silver layer 50 nm thick produces an SPR spectrum that is roughly 2 degrees wide.

The same layer when properly coated produces two different PWR spectra with the two light polarization, that are more than an order of magnitude sharper. The unique characteristics of PWR allow more information about the sample properties to be obtained at much higher sensitivities. In particular, probing optically anisotropic samples requires the capabilities that PWR offers. Thus, for anisotropic samples, the refractive index and extinction coefficient have different values for polarizations parallel and perpendicular to the sample plane, yielding information about molecular orientation within the sample.

See e.g., U.S. Pat. No. 5,521,702—Salamon, et al.— which discloses the use and formation of a biocompatible film composed of a self-assembled bilayer membrane deposited on a planar surface in connection with SPR techniques. See also, U.S. Pat. No. 5,991,488—Salamon, et al. which discloses a prism having a metallic film coated with a dielectric layer used to provide a surface plasmon wave.

Most SPR instruments do not record the SPR spectra but reduce the information to only the relative angle at which the resonance peak is detected. This approach eliminates the possibility of determining optical properties. Changes in the relative angle are assumed to correlate to changes in the refractive index of the sample layer (measured with only one polarization) due to mass moving into and out of the layer. However, relative angle measurements assume that the sample is isotropic and that the thickness and absorbance (or scattering) are constant. Unfortunately these assumptions are usually not correct in practical applications and can result in misleading data and erroneous conclusions. In addition, the molecular interactions resulting in changes in mass of the sample also usually influence the molecular organization. As an example, conformation changes occurring without net binding will result in changes in the relative angle. Further, changes in the bulk solvent will produce changes in the relative angle and can appear as binding effects. One way to avoid such misleading measurements is to use both polarizations and to analyze the full resonance spectrum.

There are a number of applications for a PWR spectrometer. For example, PWR devices can be used to probe molecular interactions (i.e. binding followed by structural alterations induced by binding) within anisotropic interfaces and thin films, including: optical coatings, lipid bilayers, proteins and peptides inserted into lipid bilayers, and others. It can also be used the way as a conventional SPR instrument to follow changes in the angular resonance peak position.

The invention is directed to improvements in PWR technology thereby yielding improved results such as more accurate measurements and increased automation of PWR systems and methods.

SUMMARY OF THE INVENTION

The invention is directed to a surface plasmon resonance system and method. The system has at least one light source operable to generate a source beam, a prism having a rear surface at least partially coated with a metallic coating, at least one layer under test, the layer under test being positioned on the rear surface of the prism, wherein the source beam is directed at the layer under test thereby defining an angle between the source beam and the rear surface of the prism. The system also has a detector operable to detect light that is reflected and/or scattered by the layer under test, wherein the source beam is directed towards the layer under test at a selected angle, and the source beam is shifted along a first plane (e.g., horizontal or vertical) to illuminate at least a portion of the layer under test based on the selected angle and the position of the layer under test on the rear surface of the prism.

In one embodiment the system has a turntable operable to rotate about an axis of rotation and adjust the angle between the source beam and the rear surface of the prism to the selected angle, wherein the prism is coupled to the turntable. In this embodiment, the system also has a mirror coupled to a linear slide (e.g., microslide), wherein the linear slide is operable to linearly displace the mirror, the mirror being operable to direct the source beam towards the prism and the linear slide being operable to shift the source beam and illuminate at least a portion of the layer under test based on the selected angle and the position of the layer under test on the rear surface of the prism.

In another embodiment the system has a steering mirror coupled to a linear slide, wherein the steering mirror is operable to rotate about an axis of rotation, wherein the linear slide is operable to linearly displace the steering mirror, the steering mirror being operable to direct the source beam towards the prism and adjust the angle between the source beam and the rear surface of the prism to the selected angle, the linear slide being operable to shift the source beam and illuminate at least a portion of the layer under test based on the selected angle and the position of the layer under test on the rear surface of the prism.

In yet another embodiment, the system has a first and second steering mirror, wherein each steering mirror is operable to rotate about an axis of rotation, wherein the first and second steering mirror are operable to direct the source beam towards the prism, adjust the angle between the source beam and the rear surface of the prism to the selected angle and shift the source beam and illuminate at least a portion of the layer under test based on the selected angle and the position of the layer under test on the rear surface of the prism.

Another aspect of the invention provides for a metallic coating on the rear surface of the prism that is at least partially coated a dielectric layer. The system can also utilize a prism that has a rear surface that is partially coated with a metallic coating, thereby defining a coated portion and an uncoated portion.

Another aspect of the invention provides for at least a first and second layer under test are formed on the rear surface of the prism. For example, a first layer under test can be formed on the coated portion and second layer under test can be formed on the uncoated portion. In the alternative, a sample layer can be formed on the coated portion and a coated reference layer can be formed on the coated portion. In yet another alternative, a sample layer can be formed on the coated portion and a bare reference layer is formed on the uncoated portion. In yet another alternative, a sample layer can be formed on the coated portion, a coated reference layer can be formed on the coated portion, and a bare reference layer can be formed on the uncoated portion.

Another preferred aspect of the invention provides for source beam shifting along a first plane (e.g., horizontal) and a second plane (e.g., vertical) so that the rear surface of the prism can be illuminated in two-dimensional array like fashion. To this end, first and second mirrors can be provided to shift the source beam along the second plane.

BRIEF DESCRIPTION OF THE DRAWINGS

FIG. 3 is a pictorial view showing an exemplary prism structure for use in accordance with the invention.

FIG. 4 is a pictorial view showing the prism structure of FIG. 3 and a sample layer in accordance with the invention.

FIG. 5 is a pictorial view showing some of the relevant angles and measurements used to determine the proper microslide motion or shift associated with a 38° selected angle in accordance with the invention.

DETAILED DESCRIPTION OF THE INVENTION

Figure 1:
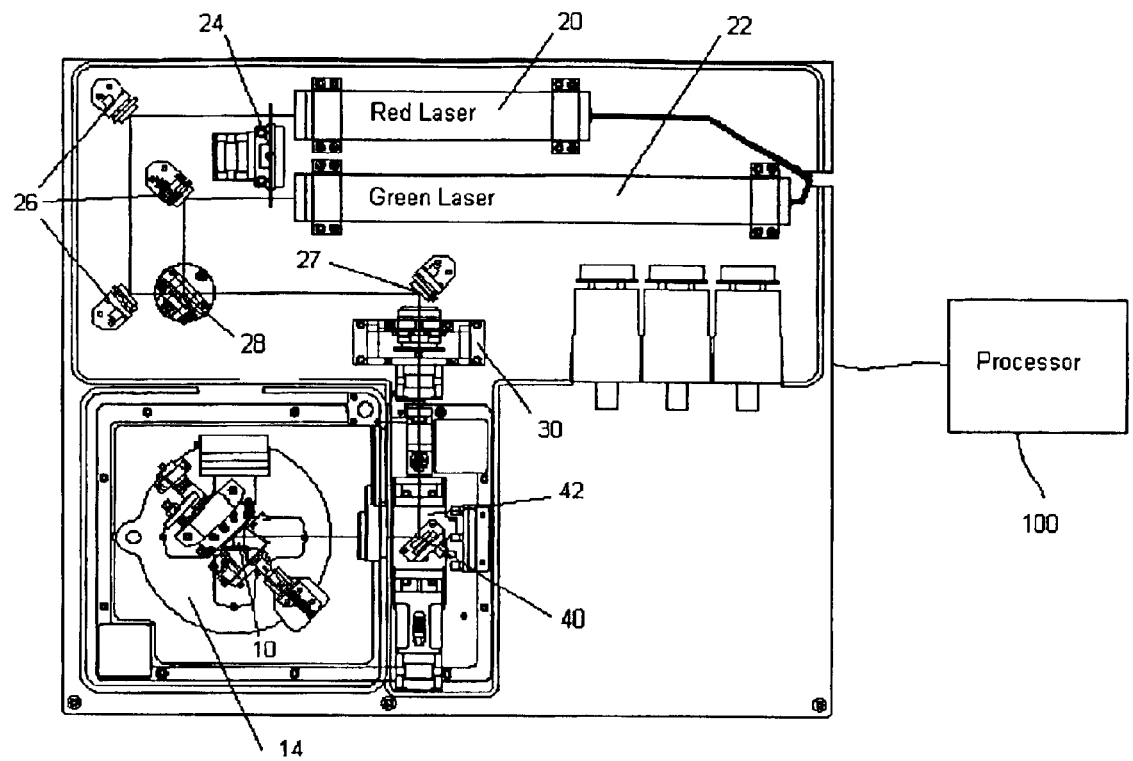
FIG. 1 is a pictorial view of a PWR device in accordance with the invention.

FIG. 1 shows a pictorial view of a surface plasmon resonance device in accordance with the invention. The device includes a prism 10 having a surface at least partially coated with thin metallic coating. For PWR applications, the prism also includes a dielectric coating applied over the metallic coating. A sample well is formed generally adjacent to the coated surface of the prism. The sample well generally supports a layer under test, for example a sample layer 12 (see FIG. 4). A layer under test can include one or more individual layers (e.g., self-assembled bilayer membrane). The layer under test generally forms a test plane that is generally adjacent and parallel to the coated surface of the prism. The prism is mounted to a turntable 14 having an axis of rotation 16 (see FIG. 2). The device also includes a light source that is generally directed towards a surface of the prism and a detector 18 (see FIG. 8) that detects reflected and/or scattered light. In a basic mode of operation, a sample layer is formed in the sample well and at least a portion of the sample layer is illuminated via the light source. The turntable is rotated and a resonance peak is detected by the detector. The selected angle between the rear surface of the prism and the incident light beam is recorded and is generally correlated with changes in the refractive index, thickness and light absorption of the layer or sample under test.

The invention also encompasses structures and methods for aiming the source beam towards a specific portion of the prism and/or layer under test during operation of the device. It is important to note that the aiming or shifting of the source beam as disclosed herein is distinct from typical calibration functions since the invention encompasses beam shifting in relation to a selected angle and the position of the layer under test on the relevant prism surface. Each time a different angle is selected, the source beam is shifted accordingly. Similarly, each time a different position for the layer under test is selected, the source beam is shifted accordingly. A preferred aspect of the invention provides for automatic (e.g., processor controlled) shifting of the source beam with respect to the prism and/or layer under test as discussed in more detail below.

Referring to FIG. 1, an exemplary light source includes red and green lasers 20, 22, operable to generate red and green laser beams. Chopper 24 is operable to select one or both laser beams from lasers 20, 22. Mirrors 26 direct the selected laser beam sources towards beam combiner 28. The resultant red, green or mixed (e.g., orange) light is then directed towards mirror 27 and then polarizer 30 such that an appropriate polarizer is optionally selectable (e.g., linear polarizer—vertical or horizontal).

The light beam is then directed towards a beam splitter which divides the light beam into essentially two portions. The first portion of the light beam is directed towards a reference detector. The second portion of the light beam (i.e., source beam) is directed towards a mirror 40 mounted to a linear slide or microslide 42. Finally, the source beam is directed towards the prism 10.

Preferably, various system components are coupled to processor 100, operable to automate various system functions as discussed below. Processor 100 can be implemented using a typical personal computer and associated operating system such as a Microsoft Windows product, Linux or the like. The hardware and software configuration of a processor operable to control and automate a PWR device in accordance with the invention based on the disclosure herein is well within the grasp of those skilled in the art.

The term "light source" as recited herein refers to source of light in its broadest sense. It is understood that a variety of different light sources can be used to produce a suitable light beam, including but not limited to, semiconductor lasers, gas lasers, solid state lasers and the like. It is also understood that a light source can include various intermediate devices, including but not limited to, optical fibers, lenses and/or mirrors for focusing, collimating, polarizing, filtering, aiming and/or altering the properties of the light beam. Accordingly, the term "light source" as recited herein is not limited to the precise arrangement shown in FIG. 1.

Figure 2:
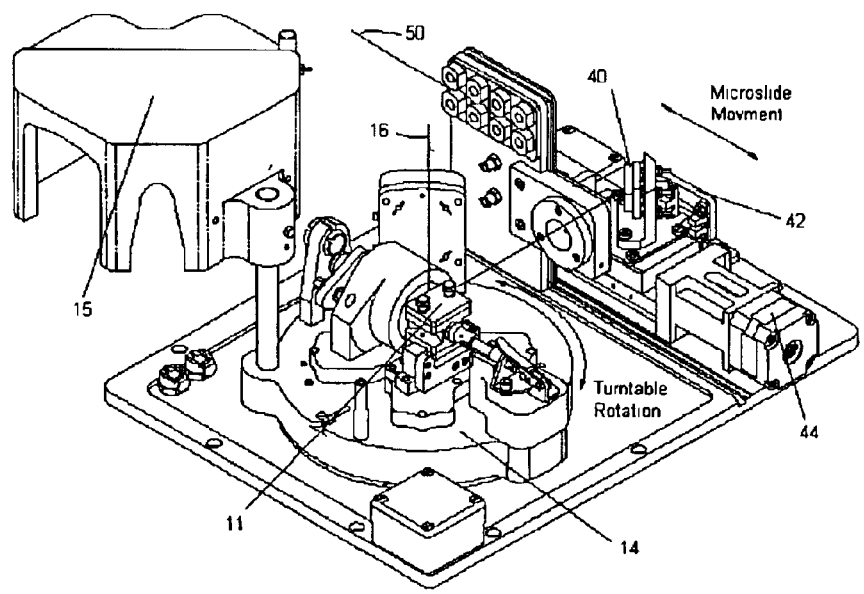
FIG. 2 is a pictorial view showing a more detailed view of a turntable, mirror and microslide in accordance with FIG. 1.

FIG. 2 shows a more detailed view of the turntable 14, mirror 40 and microslide 42. As discussed above, turntable 14 has an axis of rotation 16. Preferably, turntable 14 is coupled to a rotary drive mechanism (not shown) operable to automate rotary movement. Preferably, the rotary drive mechanism is coupled to a controller and/or processor (see e.g., FIG. 1—processor 100) operable to initiate rotary movement of the turntable and track the angle of the turntable with respect to the source beam. The tracking of selected angles, interconnection of turntables, rotary drive mechanisms and controllers and/or processors based on the disclosure herein is well within the grasp of those skilled in the art.

A linear actuator 44 is coupled to microslide 42 and is operable to move microslide 42 in precise increments as discussed in more detail below. Preferably, linear actuator 44 is coupled to a controller and/or processor (see e.g., FIG. 1—processor 100) operable to initiate movement of microslide 42 and track the relative displacement. The tracking of relative displacement, interconnection of linear slides (microslides), linear actuators controllers and/or processors based on the disclosure herein is also well within the grasp of those skilled in the art.

FIGS. 3 and 4 shows an exemplary prism structure for use in accordance with the invention. The prism 10 has an entrance surface 60, an exit surface 62 and a rear surface 64. The rear surface is at least partially coated with a metallic film 66. In the case of PWR applications, the prism is optionally coated with a dielectric layer 67 (e.g., silica dioxide). As discussed above, the two metals that produce the strongest SPR signals are gold and silver. Since PWR techniques include a dielectric layer, silver is preferable. However, other metallic layers are compatible with the invention.

Mirror 40 and microslide 42 are operable to shift the source beam direction and adjust the location at which the beam intersects the various surfaces of the prism. The invention is also operable to automatically initiate microslide movements and track the relative displacement (e.g., under processor control). Thus, the invention is operable to direct the source beam to a specific location of the prism (e.g., the entrance surface 60 and a rear surface 64 and/or sample layer in particular). The precise shift or movement required is governed by Snell's Law: when light travels from one medium to another, the angles and refractive indexes of the media determine the path that light takes. The relationship is a function of the sine of the angles (e.g., $n_1 \sin \emptyset_1 = n_2 \sin \emptyset_2$, where $n_1$ and $n_2$ are the indexes of refraction of the respective mediums and $\emptyset_1$ and $\emptyset_2$ are the incident angles of the light beams measured with respect to the interface between the two mediums).

Figure 6:
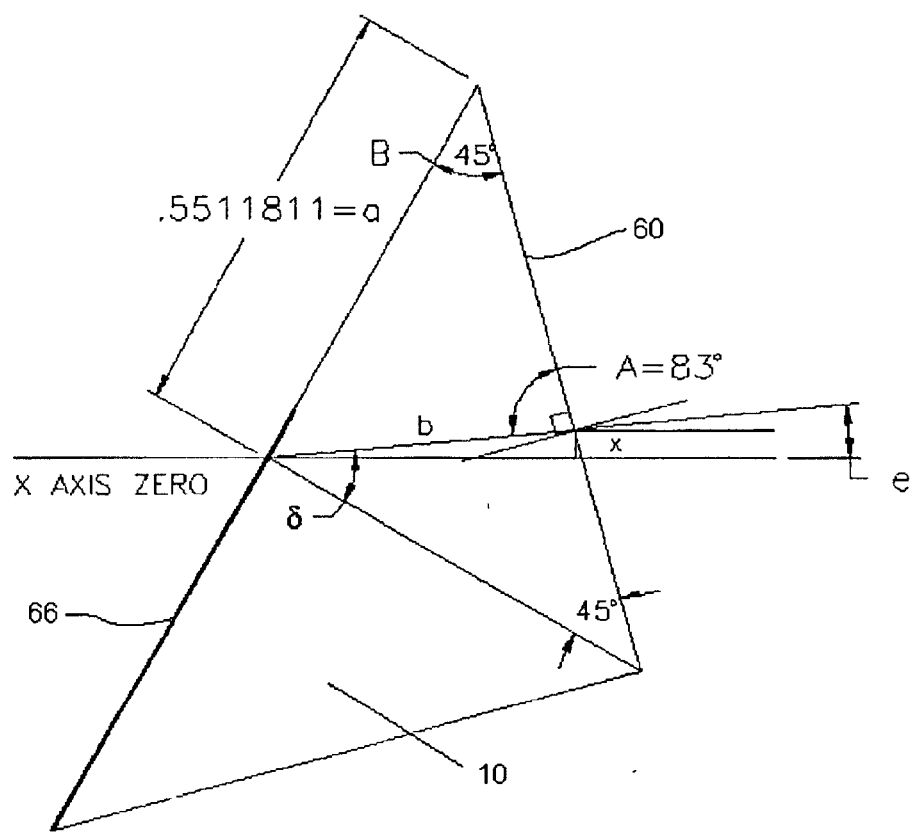
FIG. 6 is a pictorial view in accordance with FIG. 5 showing some additional angles and measurements used to determine the proper microslide motion or shift associated with a 38° selected angle in accordance with the invention.
Figure 7:
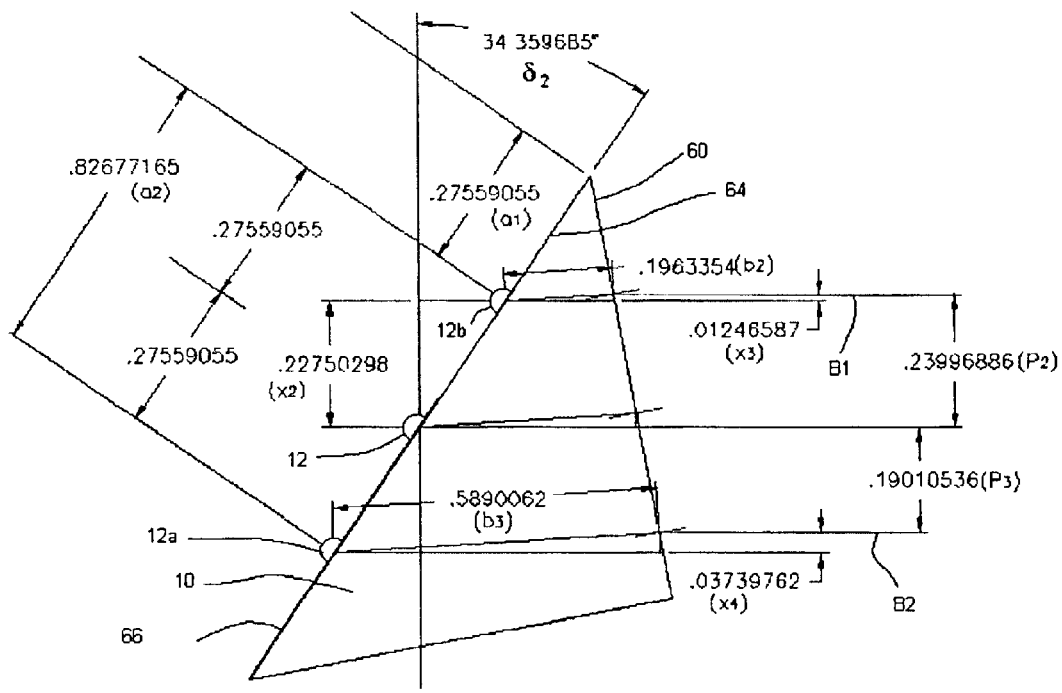
FIG. 7 is a pictorial view in accordance with FIGS. 5 and 6 showing some additional angles and measurements used to determine the proper microslide motion or shift associated with a 38° selected angle in accordance with the invention.

FIGS. 5–7 show an example in which the microslide motion or shift is determined. In this example, the desired angle of incidence between the source beam and the rear face of the prism is 38° (measured from 90° as shown). The angular position of the turntable can be determined in accordance with Snell's law (see FIG. 5). The following parameters apply:

index of refraction=1.5150892 (based on the prism used)

prism face=28 mm (1.1023622 inches)

turntable home=45° a=prism rotation from home microslide home=zero from x axis shown

Solving for a, where d is the angular displacement from home. Angle d is associated with an arithmetic sign such that a is negative for counter clockwise rotation from home and a is positive for clock-wise rotation from home.

90°−38°=52°

52°+45°=97°

90°−97°=−7°=d

Applying Snell's Law:

sin(−7)×1.5150892=sin a a=−10.6403149°

Accordingly, the turntable must be rotated 10.6403149° counter clock-wise to produce a 38° angle of incidence between the source beam and the rear face of the prism (measured from 90° as shown). Referring to FIG. 6, the displacement of the microslide (x) can be determined. The following parameters apply:

x=microslide motion from home.

45°−a=f

45°−(−10.6403149°)=55.6403149°

90°−δ−f=f

90−38°−55.6403149°=−3.64031490°=e b=a(sin B)/sin A b=0.551181102(sin 45°)/sin 83° b=0.392670804 x=b(sin E)

x=−0.024931747

Where if x is negative, microslide motion is forward. If x is positive, microslide motion is reverse.

FIG. 7 illustrates larger scale light beam shifting in accordance with the invention and shows a prism illuminated with two exemplary light beams, B1 and B2. It is understood that normal operation of the invention requires only a single light beam at any one time. Larger scale light beam shifts allow the invention to illuminate different portions of the prism (spaced apart from the x axis). This allows the invention to measure the optical characteristics of several different layers under test without user intervention. A preferred aspect of the invention also provides for multiple layers under test (e.g., multiple reference and/or sample layers).

The prism 10 has at least one surface that is partially coated with thin metallic coating. In this example, the rear surface 64 is partially coated with metallic film 66. Thus, the rear of the prism is divided into a coated portion and an uncoated portion. In this example, sample layer 12 is positioned on the coated portion generally centered on the rear surface 64 (along the x-axis). A coated reference layer 12a is also positioned on the coated portion of the metallic film 66 (at the intersection between light beam B2 and the rear surface 64). The coated reference layer is simply a dielectric layer or layers (e.g., self-assembled bilayer membrane) without any sample under test. A bare reference layer 12b is positioned on the uncoated portion of the rear surface 64 (at the intersection between light beam B1 and the rear surface 64). Similarly, the bare reference layer is simply a dielectric layer or layers (e.g., self-assembled bilayer membrane) without any sample under test. It is understood that the bare and coated references can include a variety of different chemical compositions selected to optimize the information obtained in relation to properties of the reference layers, prism, metallic coating, light source and the like.

Continuing with the example above and solving for $P_2$, the microslide shift from the home position to the bare reference position, can be accomplished as follows:

$a_1$=7 mm=0.275590551

45°+a=$\delta_2$

45°+(−10.6403149°)=34.3596851°

$x_2$=(0.275590551)cos $\delta_2$ $x_2$=0.227502982

90°−$\delta$−f=e

90°−38°−55.64031490°=−3.6403149°

$b_2$=$a_1$(sin B)/Sin A=0.275590551(sin 45°)/sin 83°

$b_2$=0.196335402

$x_3$=$b_2$(Sin e)

$x_3$=−0.012465873

$P_2$=$x_2$−($x_3$)

$P_2$=0.227502982−(−0.012465873)

$P_2$=0.239968855

If $P_2$ is positive, microslide motion is forward. If $P_2$ is negative, microslide motion is reverse. Similarly, solving for P3, the microslide shift from the home position to the coated reference position, can be accomplished as follows:

$a_2$=21 mm=0.8267711654

45°+a=$\delta_2$

45°+(−10.6403149°)=34.3596851°

$x_2$=(0.275590551)cos $\delta_2$ $x_2$=0.227502982

90°−$\delta$−f=e

90°−38°−55.6403149°=−3.64031490°=e $b_3$=$a_2$(sin B)/Sin A=0.8267711654(sin 45°)/sin 83°

$b_3$=0.589006206

$x_4$=$b_3$(Sin e)

$x_4$=0.03739762

$P_3$=−[$x_2$+($x_4$)]

$P_3$=−[0.227502982+(0.3739762)]

$P_3$=−0.1900105362

If $P_3$ is positive, microslide motion is forward. If $P_3$ is negative, microslide motion is reverse. It is understood that the calculations as set forth above are advantageously carried out by an associated controller and/or processor. It is also understood that various other system components are also advantageously coupled to the controller and/or processor (see e.g., FIG. 1—processor 100) such that the controller and/or processor is operable to initiate and coordinate the movements required to obtain any selected angle and all associated beam shifts required to illuminate the layer under test.

Figure 8:
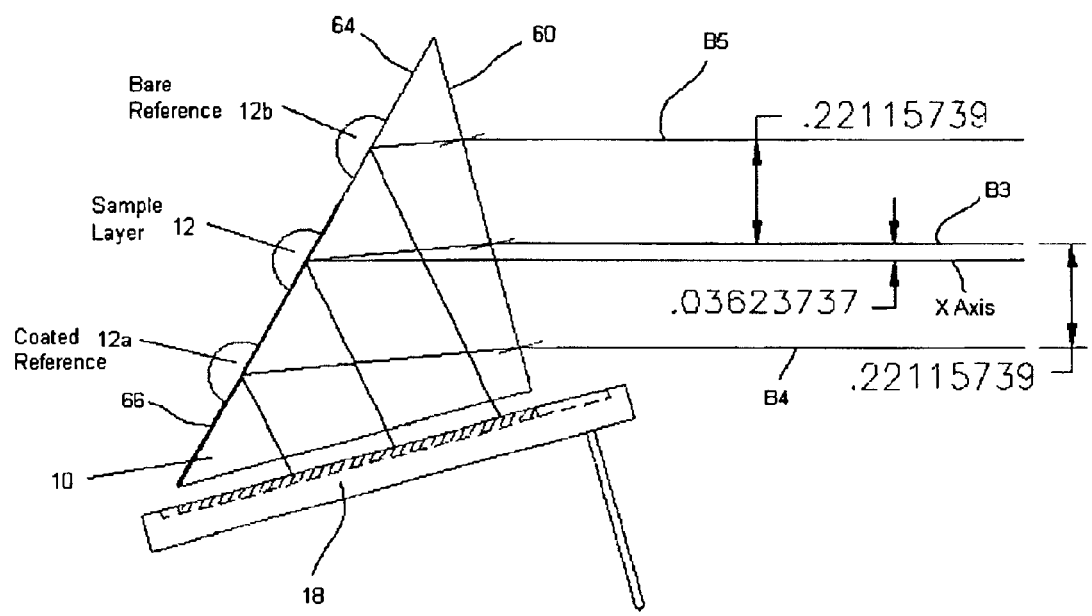
FIG. 8 is a pictorial view showing several exemplary light beams in connection with larger scale light beam shifting with a 35° incidence angle in accordance with the invention.

FIG. 8 illustrates another example with larger scale light beam shifting in accordance with the invention and shows a prism illuminated with three exemplary light beams, B3–B5. Again, the prism 10 has at least one surface that is partially coated with thin metallic coating. FIG. 8 shows the rear surface 64 partially coated with a metallic film 66. Thus, the rear of the prism is divided into a coated portion and an uncoated portion. In this example, sample layer 12 is disposed on the coated portion generally centered on the rear surface 64. A coated reference layer 12a is also disposed on the coated portion of the metallic film 66. The coated reference layer is simply a dielectric layer or layers (e.g., self-assembled bilayer membrane) without any sample under test. A bare reference layer 12b can also be formed on the uncoated portion of the rear surface 64. Similarly, the bare reference layer is simply a dielectric layer or layers (e.g., self-assembled bilayer membrane) without any sample under test.

In this example, the prism is 20 mm×20 mm×28 mm. The coated reference layer 12a and bare reference layer 12b are equally spaced from the sample layer 12 by 0.27559055 inches. The incident angle between the source beam and the rear surface 64 is 35°. Under these conditions, the microslide shift required to illuminate the sample layer 12 in the center of rear surface 64 is 0.036237 inches (the sample layer position) as set forth in more detail below.

index of refraction=1.5150892 (based on the prism used)

prism face=28 mm (1.1023622 inches)

turntable home=45° a=prism rotation from home microslide home=zero from x axis shown

Solving for a, where d is the angular displacement from home. Angle d is associated with an arithmetic sign such that a is negative for counter clockwise rotation from home and a is positive for clock-wise rotation from home.

90°−35°=55°

55°+45=100°

90°−100°=−10°=d

Applying Snell's Law:

sin(−10)×1.5150892=sin(a)

a=−15.253638°

Accordingly, the turntable must be rotated 15.253638° counter clock-wise to produce a 35° angle of incidence between the source beam and the rear face of the prism. The displacement of the microslide (x) can be determined as set forth above. The following parameters apply:

x=microslide motion from home.

45°−a=f

45°−(−15.253638°)=60.253638°

90−δ−f=e

90°−35°−60.253638°=−5.253638°=e b=a(sin B)/sin A b=0.5511811(sin 45°)/sin 80° b=0.3957563 x=b(sin E)

x=−0.036237367 (See e.g., beam B3)

Where if x is negative, microslide motion is forward. If x is positive, microslide motion is reverse.

In order to illuminate the coated reference layer 12*a* (the coated reference position—see e.g., beam B4), the microslide must be shifted to downward. Assuming the spacing between the coated reference layer 12*a* and the sample layer is 0.27559055 inches, the microslide must be shifted downward by 0.22115739 inches (with respect to the sample layer position). Similarly, illumination of the bare reference layer 12*b* (the bare reference position—see e.g., beam B5) requires an upward microslide shift. Assuming the spacing between the bare reference layer 12*b* and the sample layer is 0.27559055 inches, the microslide must be shifted upward also by 0.22115739 inches (with respect to the sample layer position). The calculations for these positions are carried out as set forth in the example above.

Figure 9:
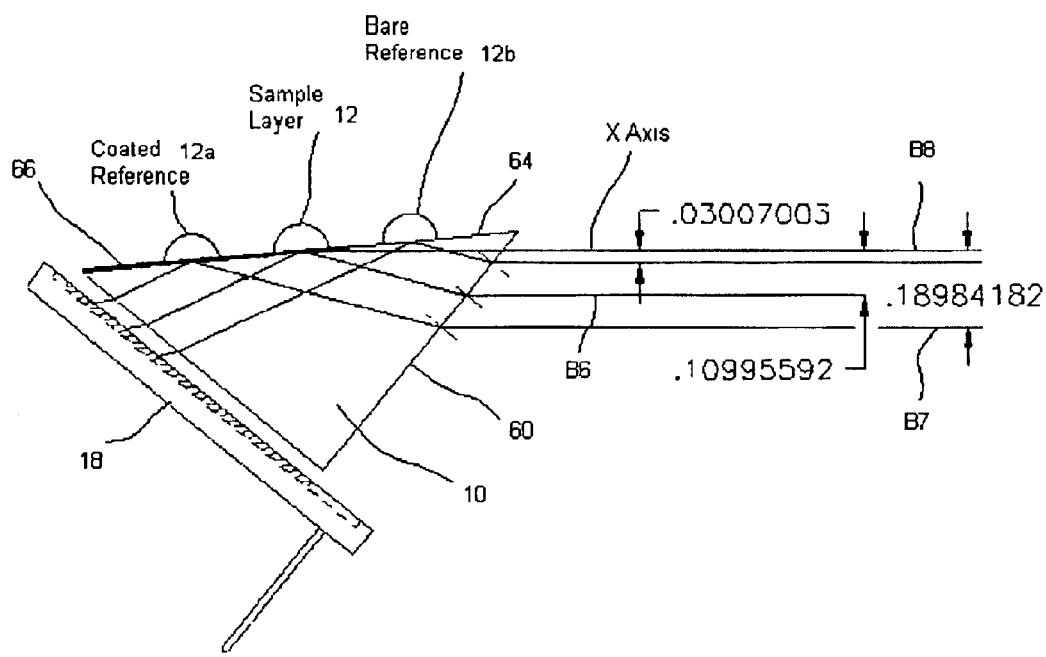
FIG. 9 is a pictorial view showing several exemplary light beams in connection with larger scale light beam shifting with a 70° incidence angle, in accordance with the invention.

FIG. 9 shows yet another example in which the incident angle between the source beam and the rear surface 64 is 70°. As in the previous examples, the rear surface 64 is partially coated with a metallic film 66, thereby defining a coated portion and an uncoated portion. In this example, sample layer 12 is disposed on the coated portion generally centered on the rear surface 64. The coated reference layer 12*a* is also disposed on the coated portion of the metallic film 66. The bare reference layer 12*b* is formed on the uncoated portion of the rear surface 64. As discussed above, the reference layers 12*a* and 12*b* are composed of a dielectric layer or layers (e.g., self-assembled bilayer membrane) without any sample under test.

In this example, the prism is again 20 mm×20 mm×28 mm. It is understood that different prism configurations and dimensions can be used without departing from the scope of the invention. The coated reference layer 12*a* and bare reference layer 12*b* are equally spaced from the sample layer 12 by 0.27559055 inches. The incident angle between the source beam and the rear surface 64 is 70°. Under these conditions, the microslide shift required to illuminate the sample layer 12 in the center of rear surface 64 (e.g., beam B6) is 0.10995592 inches.

In order to illuminate the coated reference layer 12*a* (the coated reference position, see e.g., beam B7) the microslide must be shifted to downward to illuminate the coated reference layer. Assuming the spacing between the coated reference layer 12*a* and the sample layer is 0.27559055 inches, the microslide must be shifted downward by 0.18984182 inches (with respect to the X axis). In this example, illumination of the bare reference layer 12*b* (the bare reference position, see e.g., beam B8) also requires a downward microslide shift. Assuming the spacing between the bare reference layer 12*b* and the sample layer is 0.27559055 inches, the microslide must be shifted downward by 0.03007003 inches (with respect to the X axis). The calculations for these positions are carried out as set forth in the example above.

The combination of beam shifting capabilities and the provision of one or more reference layers as well as a sample layer provides several advantages. For example, provision of a coated reference layer and a sample layer allows the device to automatically image both layers in rapid succession. Data collected from the coated reference layer can be used to generate correction factors and compensate for variations in the dielectric as well as the metallic film 66. Similarly, the provision of a bare reference layer and a sample layer allows the device the device to automatically image both layers in rapid succession. Data collected from the coated reference layer can be used to generate correction factors and compensate for variations in the dielectric as well as the optical properties of the prism. Provision of the provision of a coated reference layer, bare reference layer and a sample layer allows the device the device to automatically image all three layers in rapid succession. This allows for the generation of correction factors to compensate for variations in the dielectric, metallic film and optical properties of the prism.

A preferred aspect of the invention relates to the combination of establishing a desired incidence angle and the shifting of the source beam to illuminate a particular point on the prism surface. As explained above, beam shifting can be carried out on a small scale (e.g., small shifts for layers under test that are disposed on the x axis, largely to compensate changes in the selected angle). Beam shifting can also be carried out on a larger scale (e.g., larger shifts, largely to accommodate position changes of the layer under test). In the examples above, beam shifting is carried out with respect to three distinct positions on the rear surface of the prism (e.g., the bare reference position, the coated reference position and the sample layer position). However, the invention can be configured to address the rear surface of the prism in linear or one-dimensional array like fashion. Accordingly, the invention can be utilized to address two or more sample and/or reference positions. Accommodation of large numbers of sample and/or reference positions may require relatively close spacing between positions and/or increased prism dimensions.

Figure 10:
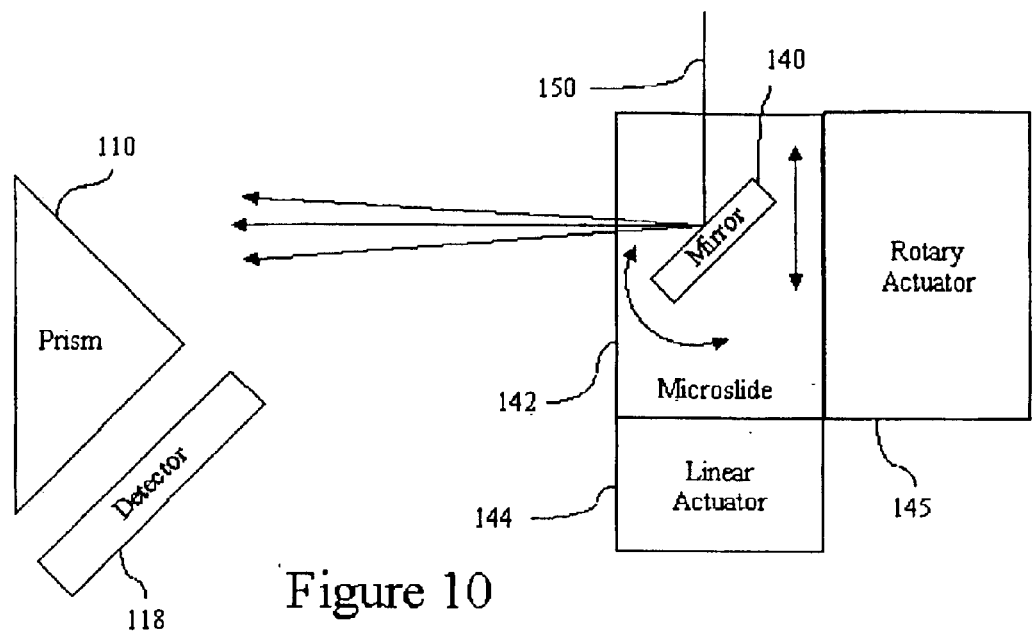
FIG. 10 is a pictorial view showing an alternate embodiment having a microslide and a steering mirror in accordance with the invention.

In the examples above, beam shifting is accomplished by the combination of a turntable and a mirror mounted to a microslide. However, a variety of other structures could be used without departing from the scope of the invention. For example, FIG. 10 shows an alternative structure in accordance with the invention. In this example, the turntable has been omitted. A steering mirror 140 is coupled to a microslide 142. The steering mirror 140 is rotatable about an axis of rotation as shown. A linear actuator 144 is coupled to microslide 142 and is operable to move microslide 142 in precise increments as discussed above. Preferably, linear actuator 144 is coupled to a controller and/or processor operable to initiate movement of microslide 142 and track the relative displacement. Steering mirror 140 is coupled to a rotary actuator 145, operable to move steering mirror 140 in precise rotary increments and track the rotary displacement. In operation, source beam 150 is directed at steering mirror 142 which can be adjusted (via linear actuator 144 and rotary actuator 145) to provide the desired incidence angle and beam shift in accordance with the invention. The tracking of displacement and the interconnection of steering mirrors, linear slides (microslides), linear actuators, rotary actuators, controllers and/or processors based on the disclosure herein is also well within the grasp of those skilled in the art. The calculations for the required rotary and linear movements of the steering mirror and microslide are well within the scope of those skilled in the art based on the disclosure herein.

Figure 11:
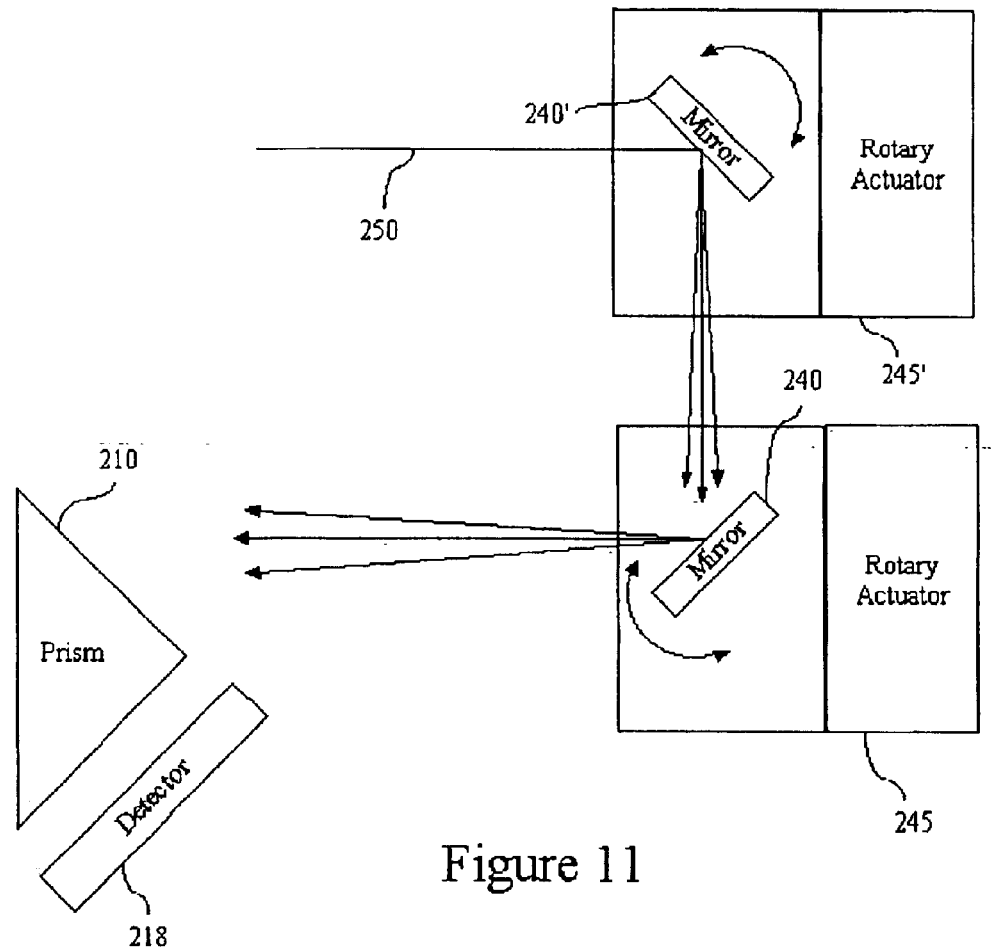
FIG. 11 is a pictorial view showing an alternate embodiment having a two steering mirrors in accordance with the invention.

FIG. 11 shows yet another alternative structure in accordance with the invention. In this example, the turntable has again been omitted. The microslide has also been omitted and two steering mirrors 240 and 240' are used. Steering mirrors 240 and 240' each have an axis of rotation and are generally rotatable as shown. Steering mirrors 240 and 240' are coupled to rotary actuators 245 and 245', both being operable to move steering mirrors 240 and 240' in precise rotary increments and track the rotary displacement. In operation, source beam 250 is directed at steering mirror 240', which can be adjusted (via linear actuator 245'). The light beam is then directed at steering mirror 240, which is also adjustable (via linear actuator 245) to ultimately provide the desired incidence angle and beam shift in accordance with the invention. As discussed above, the tracking of displacement and the interconnection of steering mirror, rotary actuators, controllers and/or processors based on the disclosure herein is also well within the grasp of those skilled in the art. It is also understood that variations and structures operable to provide a desired incidence angle and beam shift can be utilized without departing from the scope of the invention. The calculations for the required rotary movements of the two steering mirrors discussed above are well within the scope of those skilled in the art based on the disclosure herein.

In the examples above, beam shifting is carried out along a single plane (e.g., horizontally). However, the invention can be configured provide beam shifting along two distinct planes (e.g., horizontally and vertically). Accordingly, the invention can be configured to address the rear surface of the prism in two dimensional array like fashion.

Figure 12:
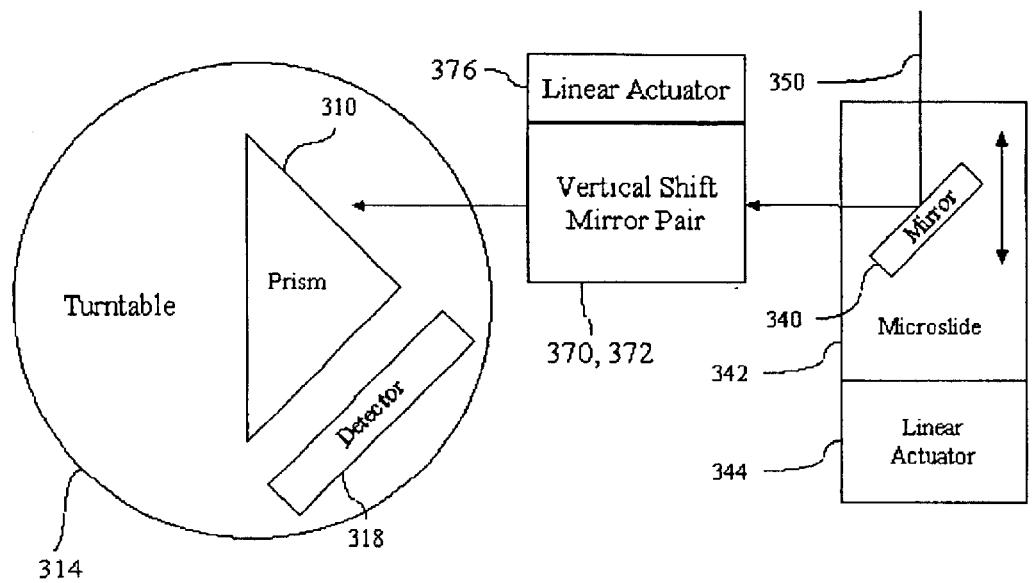
FIG. 12 is a pictorial view showing an alternate embodiment capable of two-dimensional beam shifting in accordance with the invention.

FIG. 12 shows an exemplary system operable to provide two-dimensional beam shifting. Prism 310 and detector 318 are disposed on turntable 314 much like the system shown in FIGS. 1 and 2. Mirror 340 and microslide 342 are operable to provide horizontal beam shifting (via linear actuator 344) as shown and described with respect to the system shown in FIGS. 1 and 2.

Figure 13:
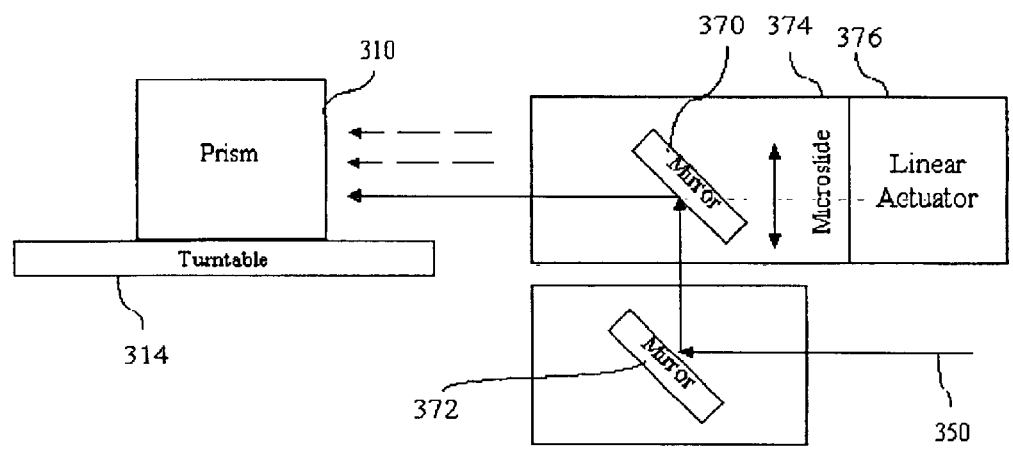
FIG. 13 is a side view of the embodiment shown in FIG. 12 in accordance with the invention.

Vertical beam shifting can be provided by a variety of structures that are readily apparent to those skilled in the art based on the disclosure herein. In the example shown in FIG. 12, a pair of mirrors (vertical shift mirror pair) are disposed along the light path to provide vertical beam shifting. FIGS. 12 and 13 show the vertical shift mirror pair disposed between mirror 340 and the prism 310. It is understood that vertical beam shifting structures can be disposed virtually anywhere along the light path without departing from the scope of the invention.

FIG. 13 shows a side view of the system of FIG. 12. Mirrors 370 and 372 are disposed within the light path and are generally spaced apart by a distance that is correlated to the desired vertical beam shift. The source beam 350 is reflected vertically by mirror 372 (in this case a stationary mirror). Mirror 370 is coupled to a linear actuator and is generally disposed above mirror 372. The source beam is reflected in the horizontal direction by mirror 370. Preferable a linear actuator 376 is coupled to microslide 374 and is operable to move microslide 374 in precise increments to select the desired vertical beam shift. Preferably, linear actuator 376 is coupled to a controller and/or processor operable to initiate movement of microslide 374 and track the displacement of mirrors 370 and 372. The tracking of displacement and the interconnection of linear slides (microslides), linear actuators controllers and/or processors based on the disclosure herein is also well within the grasp of those skilled in the art.

Figure 14:
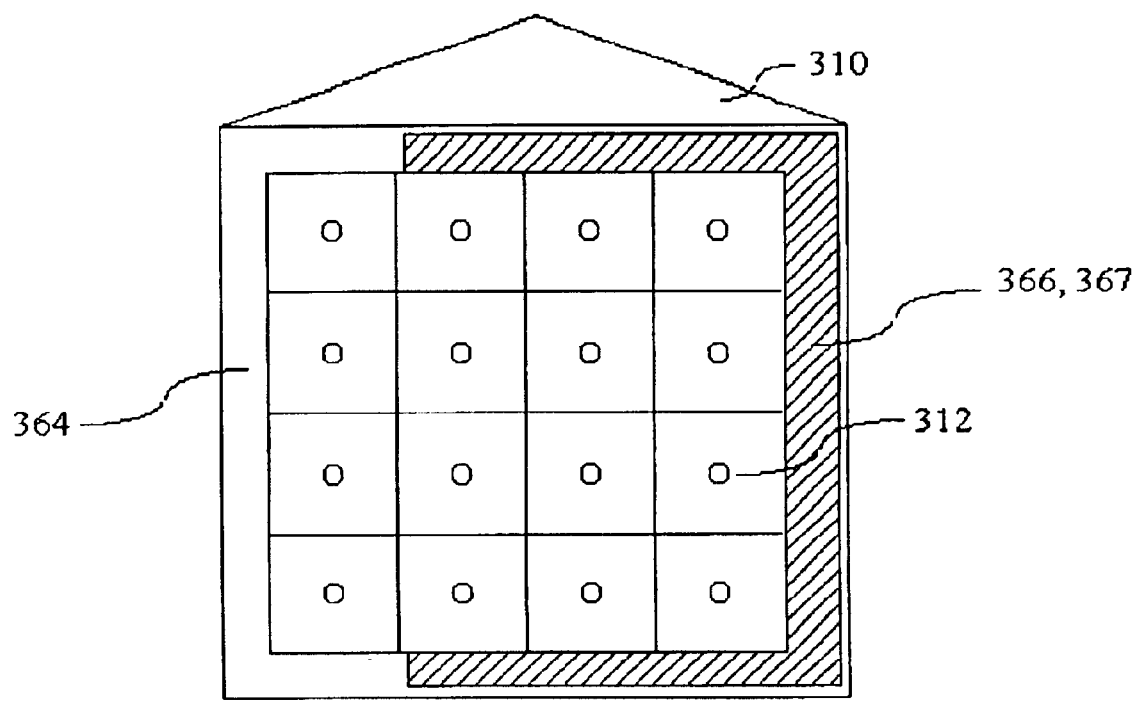
FIG. 14 is pictorial view of a prism used in conjunction with the embodiment shown in FIGS. 12 and 13 in accordance with the invention.

FIG. 14 shows an exemplary prism 310, used in conjunction with the two dimensional beam shifting system discussed above. The rear surface of the prism 364 has been arbitrarily divided into a 4×4 array for 16 sample and/or reference layers. As discussed above, the rear surface of the prism 364 can be partially coated with a metallic film 366. In the case of PWR applications, the prism is optionally coated with a dielectric layer 67. Addressing of the sample and/or reference layers in row-like fashion (horizontally) is accomplished via mirror 340 and its associated microslide (as discussed in connection with the system shown FIGS. 1 and 2). Addressing of the sample and/or reference layers in column-like fashion is accomplished via the vertical shift mirror pair. Linear displacement of mirror 370 results in a directly proportional and corresponding vertical beam shift.

In the example above, beam shifting is carried out with respect to 16 distinct positions on the rear surface of the prism. It is understood that other array dimensions can be accommodated without departing from the scope of the invention. As discussed above, accommodation of large numbers of sample and/or reference positions may require relatively close spacing between positions and/or increased prism dimensions. It is also understood that other structures can be utilized to implement the two-dimensional beam shifting in accordance with the invention.

Figure 15:
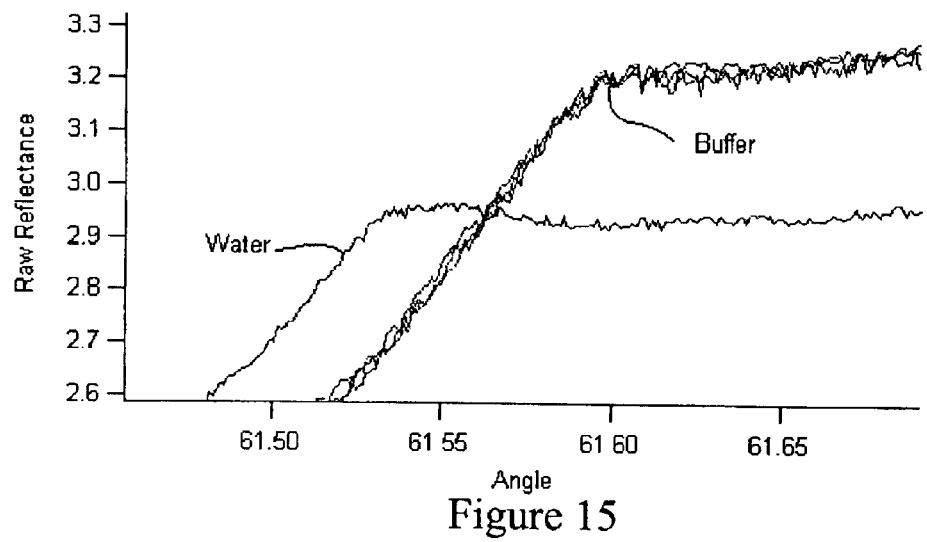
FIG. 15 is a graph showing exemplary graph of raw reflectance plotted against selected angle for two different layers under test in accordance with the invention.
Figure 16:
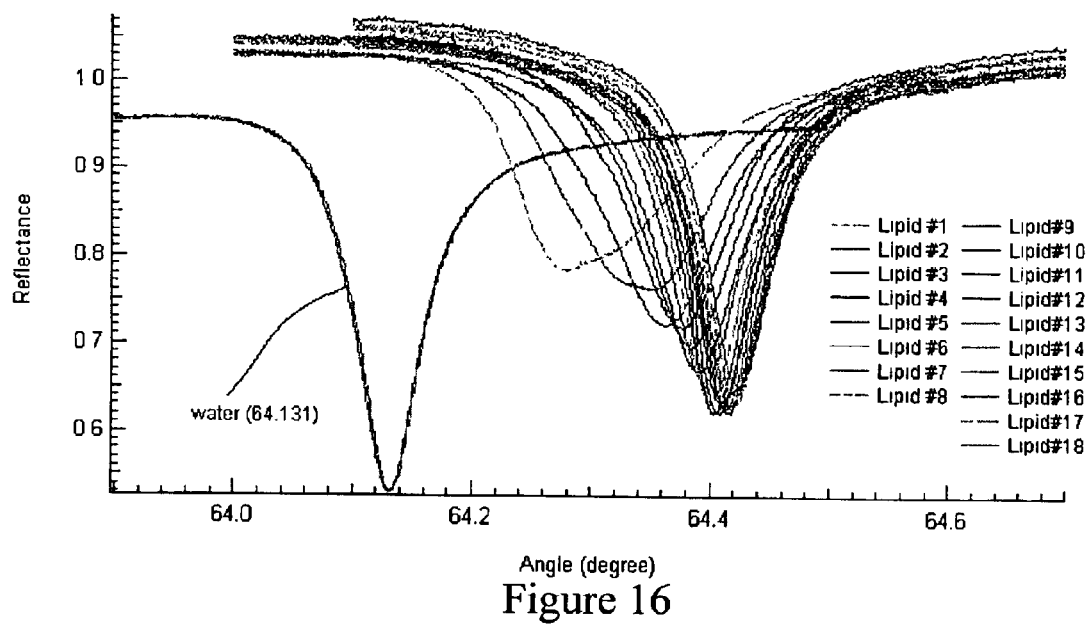
FIG. 16 is a graph showing exemplary graph of reflectance plotted against selected angle for various layers under test in accordance with the invention.

FIG. 15 is an exemplary graph produced in accordance with the invention. In this example, raw reflectance of bare reference is plotted against the selected angle for two different layers under test (water and a buffer). FIG. 16 is yet another is an exemplary graph produced in accordance with the invention. In this example, reflectance of the sample position is plotted against the selected angle for various layers under test. The left most curve (water) shows a null at approximately 64.131° The remaining curves (various lipid bilayers) have nulls that falling approximately in the 64.26° to 64.42° range. The results shown in FIGS. 15 and 16 generally illustrate the level of precision that is realized utilizing the structures and methods disclosed herein. A more detailed analysis of these graphs is beyond the scope of this disclosure.

While this invention has been described with an emphasis upon preferred embodiments, it will be obvious to those of ordinary skill in the art that variations in the preferred devices and methods may be used and that it is intended that the invention may be practiced otherwise than as specifically described herein.

What is claimed is:

1. A surface plasmon resonance system comprising:
   at least one light source operable to generate a source beam,
   a prism having a rear surface at least partially coated with a metallic coating,
   at least one layer under test positioned on the rear surface of the prism, wherein the source beam is directed at the layer under test thereby defining an angle between the source beam and the rear surface of the prism,
   a detector operable to detect light that is at least one of reflected and scattered by the layer under test, wherein the source beam is directed towards the layer under test at a selected angle, and the source beam is shifted along a first plane to illuminate at least a portion of the layer under test based on the selected angle and the position of the layer under test on the rear surface of the prism,
   a turntable operable to rotate about an axis of rotation and adjust the angle between the source beam and the rear surface of the prism to the selected angle, wherein the prism is coupled to the turntable, and
   a mirror coupled to a linear slide, wherein the linear slide is operable to linearly displace the mirror, the mirror being operable to direct the source beam towards the prism and the linear slide being operable to shift the source beam and illuminate at least a portion of the layer under test based on the selected angle and the position of the layer under test on the rear surface of the prism.

2. The system of claim 1 wherein at least a first and second layer under test are formed on the rear surface of the prism.

3. The system of claim 1 wherein the source beam is shifted along a first plane and a second plane so that the rear surface of the prism can be illuminated in two-dimensional array like fashion.

4. The system of claim 3 comprising:
first and second mirrors operable to shift the source beam along a second plane.

5. The system of claim 1 wherein the metallic coating on the rear surface of the prism is at least partially coated a dielectric layer.

6. The system of claim 1 comprising:
a first and second steering mirror, wherein each steering mirror is operable to rotate about an axis of rotation, wherein the first and second steering mirror are operable to direct the source beam towards the prism, adjust the angle between the source beam and the rear surface of the prism to the selected angle and shift the source beam and illuminate at least a portion of the layer under test based on the selected angle and the position of the layer under test on the rear surface of the prism.

7. The system of claim 1 wherein the prism has a rear surface that is partially coated with a metallic coating, thereby defining a coated portion and an uncoated portion.

8. The system of claim 7 wherein a first layer under test is fanned on the coated portion and second layer under test is formed on the uncoated portion.

9. The system of claim 7 wherein a sample layer is formed on the coated portion and a coated reference layer is formed on the coated portion.

10. The system of claim 7 wherein a sample layer is fanned on the coated portion and a bare reference layer is formed on the uncoated portion.

11. The system of claim 7 wherein a sample layer is formed on the coated portion, a coated reference layer is formed on the coated portion, and a bare reference layer is formed on the uncoated portion.

12. The system of claim 1 comprising:
a steering mirror coupled to a linear slide, wherein the steering mirror is operable to rotate about an axis of rotation, wherein the linear slide is operable to linearly displace the steering mirror, the steering mirror being operable to direct the source beam towards the prism and adjust the angle between the source beam and the rear surface of the prism to the selected angle, the linear slide being operable to shift the source beam and illuminate at least a portion of the layer under test based on the selected angle and the position of the layer under test on the rear surface of the prism.

13. A surface plasmon resonance method comprising:
providing a prism having a rear surface at least partially coated with a metallic coating,
providing at least one layer under test positioned on the rear surface of the prism,
directing a source beam at the layer under test at a selected angle between the source beam and the rear surface of the prism,
shifting the source beam to illuminate a specific portion of the layer under test based on the selected angle and the position of the layer under test on the rear surface of the prism,
providing a turntable operable to rotate about an axis of rotation and adjust the angle between the source beam and the rear surface of the prism to the selected angle, wherein the prism is coupled to the turntable, and
providing a mirror coupled to a linear slide, wherein the linear slide is operable to linearly displace the mirror, the mirror being operable to direct the source beam towards the prism and the linear slide being operable to shift the source beam and illuminate at least a portion of the layer under test based on the selected angle and the position of the layer under test on the rear surface of the prism.

14. The method of claim 13 herein the source beam is shifted along a first plane and a second plane so that the rear surface of the prism can be illuminated in two-dimensional array like fashion.

15. The method of claim 14 comprising:
providing first and second mirrors operable to shift the source beam along a second plane.

16. The method of claim 13 comprising:
providing a steering mirror coupled to a linear slide, wherein the steering mirror is operable to rotate about an axis of rotation, wherein the linear slide is operable to linearly displace the steering mirror, the steering mirror being operable to direct the source beam towards the prism and adjust the angle between the source beam and the rear surface of the prism to the selected angle, the linear slide being operable to shift the source beam and illuminate at least a portion of the layer under test based on the selected angle and the position of the layer under test on the rear surface of the prism.

17. The method of claim 13 comprising:
providing a first and second steering minor, wherein each steering mirror is operable to rotate about an axis of rotation, wherein the first and second steering mirror are operable to direct the source beam towards the prism, adjust the angle and adjust the angle between the source beam and the rear surface of the prism to the selected angle and shift the source beam and illuminate at least a portion of the layer under test based on the selected angle and the position of the layer under test on the rear surface of the prism.

18. The method of claim 13 wherein the metallic coating on the rear surface of the prism is at least partially coated a dielectric layer.

19. The method of claim 13 wherein at least a first and second layer under test are formed on the rear surface of the prism.

20. The method of claim 13 wherein the prism has a rear surface that is partially coated with a metallic coating, thereby defining a coated portion and an uncoated portion.

21. The method of claim 20 wherein a first layer under test is formed on the coated portion and second layer under test is formed on the uncoated portion.

22. The method of claim 20 wherein a sample layer is formed on the coated portion and a coated reference layer is formed on the coated portion.

23. The method of claim 20 wherein a sample layer is formed on the coated portion and a bare reference layer is formed on the uncoated portion.

24. The method of claim 20 wherein a sample layer is formed on the coated portion, a coated reference layer is formed on the coated portion, and a bare reference layer is formed on the uncoated portion.

25. A surface plasmon resonance system comprising:
at least one light source operable to generate a source beam, a prism having a rear surface at least partially coated with a metallic coating, at least one layer under test positioned on the rear surface of the prism, wherein the source beam is directed at the layer under test thereby defining an angle between the source beam and the rear surface of the prism, a detector operable to detect light that is at least one of reflected and scattered by the layer under test, a turntable operable to rotate about an axis of rotation and adjust the angle between the source beam and the rear surface of the prism to a selected angle, wherein the prism is coupled to the turntable, and a mirror coupled to a linear slide, wherein the linear slide is operable to linearly displace the mirror, the mirror being operable to direct the source beam towards the prism and the linear slide being operable to shift the source beam along a first plane and illuminate at least a portion of the layer under test based on the selected angle and the position of the layer under test on the rear surface of the prism.

26. The system of claim 25 wherein the source beam is shifted along a first plane and a second plane so that the rear surface of the prism can be illuminated in two-dimensional array like fashion.

27. The system of claim 26 comprising:

first and second mirrors operable to shift the source beam along a second plane.

* * * * *